US010610082B2

(12) United States Patent
Tanaka et al.

(10) Patent No.: US 10,610,082 B2
(45) Date of Patent: Apr. 7, 2020

(54) ENDOSCOPE APPARATUS (71) Applicant: OLYMPUS CORPORATION, Tokyo (JP)

(72) Inventors: Satoshi Tanaka, Hachioji (JP); Tomoya Takahashi, Hachioji (JP); Takahiro Masaki, Kawasaki (JP); Kazue Hongo, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 412 days.

(21) Appl. No.: 15/473,927

(22) Filed: Mar. 30, 2017

(65) Prior Publication Data
US 2017/0202431 A1 Jul. 20, 2017

Related U.S. Application Data (63) Continuation of application No. PCT/JP2015/075517, filed on Sep. 8, 2015.

(30) Foreign Application Priority Data

Feb. 4, 2015 (JP) .................................. 2015-020622

(51) Int. Cl.
A61B 1/00 (2006.01)
A61B 1/06 (2006.01)
(Continued)

(52) U.S. Cl.
CPC ...... A61B 1/00006 (2013.01); A61B 1/00009 (2013.01); A61B 1/00114 (2013.01);
(Continued)

(58) Field of Classification Search
CPC combination set(s) only.
See application file for complete search history.

(56) References Cited

U.S. PATENT DOCUMENTS

2004/0210112 A1* 10/2004 Ota ...................... A61B 1/0669
600/180
2008/0170846 A1* 7/2008 Wang ................. A61B 1/00096
396/182
(Continued)

FOREIGN PATENT DOCUMENTS

CN 104768271 A * 7/2015
EP 2449951 A1 5/2012
(Continued)

OTHER PUBLICATIONS

International Search Report dated Nov. 10, 2015 issued in PCT/JP2015/075517.
(Continued)

Primary Examiner — John P Leubecker
Assistant Examiner — Shankar Raj Ghimire
(74) Attorney, Agent, or Firm — Scully, Scott, Murphy & Presser, P.C.

(57) ABSTRACT

An endoscope apparatus includes: a first semiconductor light-emitting element; a light source drive section; a first detection section; a storage section configured to store a threshold value indicating whether or not the first detection section can correctly detect an intensity; and a control section configured to, if the intensity detected by the first detection section exceeds the threshold value stored in the storage section, control the current value of the drive signal based on the intensity detected by the first detection section, for the light source drive section, and if the intensity detected by the first detection section does not exceed the threshold value, perform control so as to make the current value of the drive signal constant to provide pulsed light emission and change a duty cycle or a number of pulses to perform light adjustment, for the light source drive section.

3 Claims, 4 Drawing Sheets (51) Int. Cl.
*G02B 23/26* (2006.01)
*A61B 1/04* (2006.01)
*G02B 23/24* (2006.01)

(52) U.S. Cl.
CPC .............. *A61B 1/04* (2013.01); *A61B 1/06* (2013.01); *A61B 1/0684* (2013.01); *G02B 23/243* (2013.01); *G02B 23/2461* (2013.01); *G02B 23/2484* (2013.01); *G02B 23/26* (2013.01)

(56) References Cited

U.S. PATENT DOCUMENTS

| | | | | |
|---|---|---|---|---|
| 2009/0033808 | A1* | 2/2009 | Maeda | G03B 33/06 348/756 |
| 2009/0033885 | A1* | 2/2009 | Shirai | G02B 26/0841 353/85 |
| 2009/0036743 | A1* | 2/2009 | Yabe | A61B 1/00009 600/180 |
| 2009/0128883 | A1* | 5/2009 | Endo | G02B 26/0841 359/290 |
| 2012/0053434 | A1* | 3/2012 | Saito | A61B 1/00009 600/324 |
| 2012/0116157 | A1* | 5/2012 | Seto | A61B 1/00057 600/109 |
| 2013/0053642 | A1* | 2/2013 | Mizuyoshi | A61B 1/00006 600/109 |
| 2014/0052004 | A1* | 2/2014 | D'Alfonso | A61B 1/0669 600/476 |
| 2014/0180004 | A1* | 6/2014 | Yamashita | A61B 1/0638 600/109 |
| 2014/0371535 | A1* | 12/2014 | Seto | A61B 1/0661 600/160 |
| 2015/0022568 | A1* | 1/2015 | Ishii | G03B 21/2013 345/697 |

FOREIGN PATENT DOCUMENTS

| | | |
|---|---|---|
| EP | 2561798 A1 | 2/2013 |
| EP | 2 702 928 A1 | 3/2014 |
| EP | 2 976 989 A1 | 1/2016 |
| EP | 3 011 892 A1 | 4/2016 |
| EP | 3 178 372 A1 | 6/2017 |
| JP | 2012-100834 A | 5/2012 |
| JP | 2013-042854 A | 3/2013 |
| JP | 5393935 B1 | 1/2014 |
| WO | WO 2015/005277 A1 | 1/2015 |

OTHER PUBLICATIONS

Extended Supplementary European Search Report dated Apr. 20, 2018 in European Patent Application No. 15 88 1151.3.

* cited by examiner

ENDOSCOPE APPARATUS

CROSS REFERENCE TO RELATED APPLICATION

This application is a continuation application of PCT/JP2015/075517 filed on Sep. 8, 2015 and claims benefit of Japanese Application No. 2015-020622 filed in Japan on Feb. 4, 2015, the entire contents of which are incorporated herein by this reference.

BACKGROUND OF THE INVENTION

1. Field of the Invention

The present invention relates to an endoscope apparatus and specifically relates to an endoscope apparatus capable of properly controlling a multiplexing ratio of light from a plurality of semiconductor light-emitting elements.

2. Description of the Related Art

Conventionally, endoscope-equipped endoscope apparatuses in which an elongated endoscope is inserted into, e.g., a body cavity to perform observation of a site to be examined or various treatments have widely been used. In such endoscope apparatuses, a light source apparatus is employed for shooting the inside of a body cavity. In recent years, in an endoscope apparatus, a light source apparatus employing semiconductor light-emitting elements such as LEDs is sometimes used as a light-emitting section.

Such endoscope apparatus includes a plurality of semiconductor light-emitting elements configured to emit light in different wavelength bands, respectively, and outputs multiplexed light resulting from the light of the plurality of colors being arbitrarily multiplexed according to, e.g., an observation mode. For example, Japanese Patent No. 5393935 discloses an endoscope apparatus that includes a red LED, a green LED and a blue LED, and multiplexes red light, green light and blue light emitted from the respective LEDs to output white light.

An endoscope apparatus includes optical sensors disposed adjacent to respective LEDs and performs feedback control to achieve favorable observation and provide a favorable endoscopic image when multiplexed light of light of a plurality of colors is outputted.

SUMMARY OF THE INVENTION

An endoscope apparatus according to an aspect of the present invention includes: a first semiconductor light-emitting element configured to generate light having an intensity according to a current value of an inputted drive signal; a light source drive section configured to input the drive signal to the first semiconductor light-emitting element; a first detection section configured to receive a part of the light generated from the first semiconductor light-emitting element and detects the intensity; a storage section configured to store a threshold value indicating whether or not the first detection section can correctly detect an intensity, which is detected by the first detection section; and a control section configured to, if the intensity detected by the first detection section exceeds the threshold value stored in the storage section, control the current value of the drive signal based on the intensity detected by the first detection section, for the light source drive section, and if the intensity detected by the first detection section does not exceed the threshold value, perform control so as to make the current value of the drive signal constant to provide pulsed light emission and change a duty cycle or a number of pulses to perform light adjustment, for the light source drive section.

DETAILED DESCRIPTION OF THE PREFERRED EMBODIMENT(S)

Embodiments of the present invention will be described in detail with reference to the drawings.

First Embodiment

Figure 1:
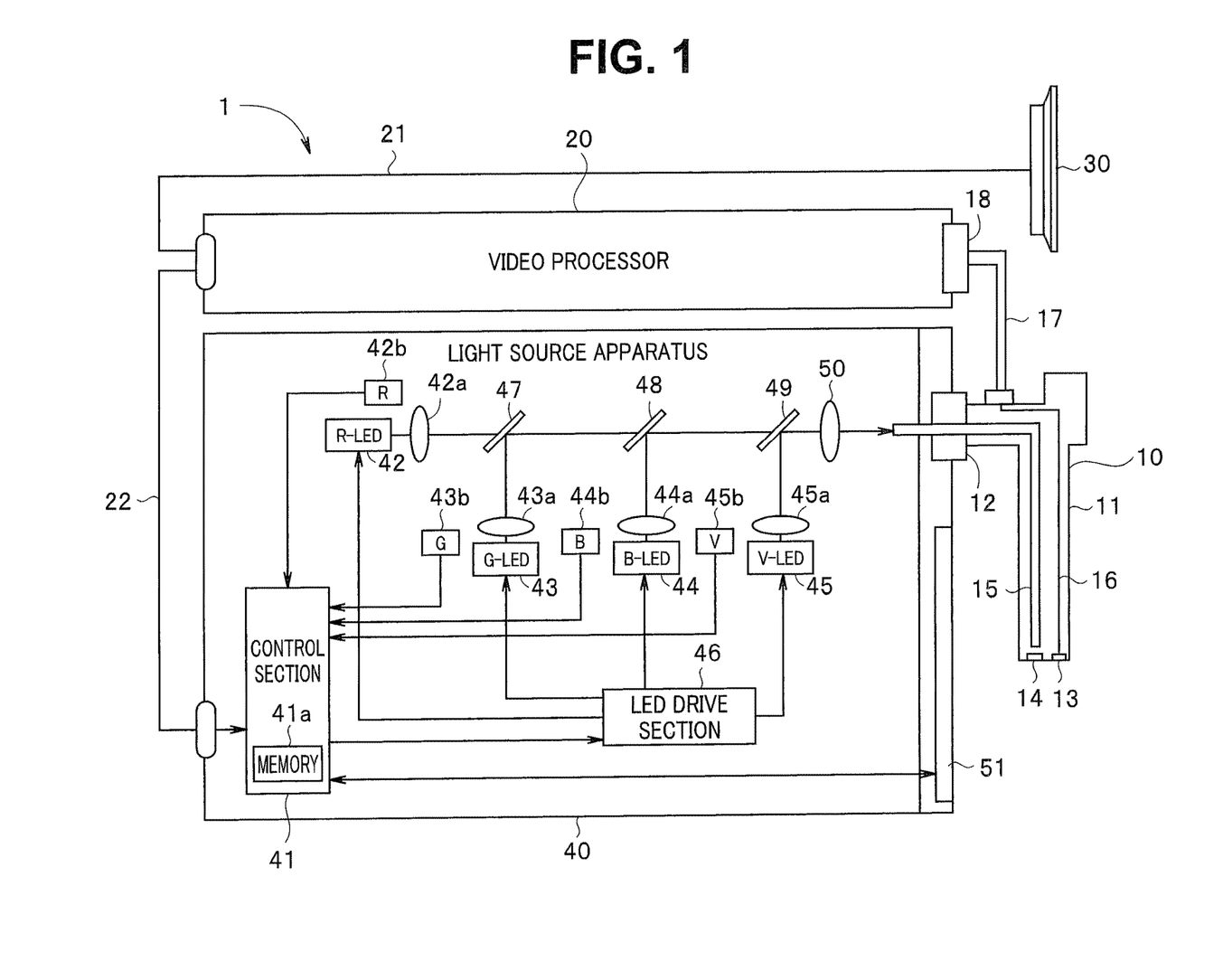
FIG. 1 is a block diagram illustrating a configuration of an endoscope apparatus according to a first embodiment.

FIG. 1 is a block diagram illustrating a configuration of an endoscope apparatus according to a first embodiment. As illustrated in FIG. 1, an endoscope apparatus 1 includes an endoscope 10, a video processor 20, a monitor 30 and a light source apparatus 40. The endoscope 10 includes an elongated insertion portion 11 on the distal end side, which can be inserted into, e.g., a lumen, and the proximal end side of the endoscope 10 is detachably connectable to the light source apparatus 40 via a connector 12.

Also, the endoscope 10 is detachably connectable to the video processor 20 via a cable 17 and a connector 18. As described above, any of different types of endoscopes can be attached to the light source apparatus 40 and the video processor 20.

In a distal end of the insertion portion 11, an image pickup device 13 for picking up an image of an object such as the inside of a lumen and a lens 14 for irradiating the object with light from the light source apparatus 40 are arranged. The lens 14 allows illuminating light transmitted from the light source apparatus 40 via a light guide 15 to irradiate the object. The image pickup device 13 includes, e.g., a CCD or CMOS sensor, and allows return light from the object to enter an image pickup surface, performs photoelectric conversion of the entered optical image of the object and sequentially outputs an image pickup output based on accumulated charges.

The image pickup device 13 operates upon being supplied with a drive signal including a synchronization signal from the video processor 20, and supplies the image pickup output to the video processor 20 via a signal wire 16.

The video processor 20 subjects the image pickup output to predetermined signal processing to produce a video signal that can be displayed on the monitor 30. The video signal from the video processor 20 is supplied to the monitor 30 via a cable 21. Consequently, on a display screen of the monitor 30, an endoscopic image based on the image pickup output can be displayed.

Also, the video processor 20 is capable of controlling the light source apparatus 40 so that a brightness of a picked-up image reaches a target brightness. The video processor 20 is configured to output information on a ratio between a brightness obtained from a picked-up image and a target brightness to the light source apparatus 40 as brightness control information. The brightness control information is supplied to a control section 41 of the light source apparatus 40 via a cable 22.

The light source apparatus 40 includes an LED (R-LED) 42 configured to generate red light, an LED (G-LED) 43 configured to generate green light, an LED (B-LED) 44 configured to generate blue light and an LED (V-LED) 45 configured to generate violet light. As described above, the LEDs 42 to 45 configuring a plurality of semiconductor light-emitting elements emit illuminating light of different colors (different wavelengths) for illuminating an object, respectively.

In the present embodiment, a plurality of different observation modes such as a normal observation mode and a narrow band light observation (narrow band imaging: NBI) are provided. These observation modes can be switched from one to another by operating, by an operator, an operation panel 51 provided at the light source apparatus 40. In the normal observation mode, the LEDs 42, 43 and 44 are lit in a predetermined color balance and white light for normal observation is emitted. On the other hand, in the narrow band light observation mode, the LED 43 for green light and the LED 45 for violet light are lit in a predetermined color balance and special light for narrow band light observation is emitted.

Here, although in the present embodiment, an example in which the four LEDs 42 to 45 configured to generate light of the four colors are employed will be described, the color types and the number of colors are not limited to the color types and the number of colors in the present embodiment. In the present embodiment, it is only necessary that plural types of LEDs be used, and for example, an LED configured to generate umber light may be added in FIG. 1.

On respective optical axes of emitted light from the respective LEDs 42 to 45, respective lenses 42*a* to 45*a* are disposed. The respective lenses 42*a* to 45*a* convert emitted light from the respective LEDs 42 to 45 into substantially-collimated light and output the substantially-collimated light. On the optical axis of the lens 42*a* configured to output light from the R-LED 42, dichroic filters 47 to 49 are disposed. Light from the G-LED 43 also enters the dichroic filter 47 via the lens 43*a*. Also, light from the B-LED 44 enters the dichroic filter 48 via the lens 44*a*, and light from the V-LED 45 enters the dichroic filter 49 via the lens 45*a*.

The dichroic filter 47 reflects light from the G-LED 43 and transmits light from the R-LED 42. Likewise, the dichroic filter 48 reflects light from the B-LED 44 and transmits the transmitted light from the dichroic filter 47. Likewise, the dichroic filter 49 reflects light from the V-LED 45 and transmits the transmitted light from the dichroic filter 48.

Consequently, light from the LEDs 42 to 45 is combined (multiplexed) by the dichroic filters 47 to 49, which are optical members. Combined light from the dichroic filter 49 enters the light guide 15 via a lens 50. Here, although the arrangement order of the LEDs 42 to 45 can be changed by arbitrarily setting characteristics of the dichroic filters 47 to 49, setting the characteristics of the dichroic filters is easier where the LEDs 42 to 45 are disposed in a wavelength band order of emitted light.

The respective LEDs 42 to 45 are lit upon the LEDs 42 to 45 being driven by the LED drive section 46. The LED drive section 46 is controlled by the control section 41 to generate drive signals for driving the respective LEDs 42 to 45. Here, each of the LEDs 42 to 45 emits an amount of light according to a current value and a duty cycle of PWM pulses of the relevant drive signal from the LED drive section 46. The control section 41 outputs light adjustment information for controlling the respective LEDs 42 to 45 to the LED drive section 46 to control the current values and the duty cycles of PWM pulses and thus performs light adjustment control of the respective LEDs 42 to 45.

Also, optical sensors 42*b* to 45*b* are disposed at respective positions at which the optical sensors 42*b* to 45*b* can detect emitted light from the respective LEDs 42 to 45. The optical sensors 42*b* to 45*b*, which serve as detection sections, detect respective intensities of illuminating light of the respective colors from the respective LEDs 42 to 45 and output respective results of the detection to the control section 41. Note that the respective optical sensors 42*b* to 45*b* are disposed at respective positions that are off respective optical paths from the respective LEDs 42 to 45 to the lenses 42*a* to 45*a*.

If sensor values from the optical sensors 42*b* to 45*b* are equal to or greater than respective predetermined values, the control section 41 controls current values of the LEDs 42 to 45 based on the sensor values from the optical sensors 42*b* to 45*b* and information stored in a memory 41*a*, which will be described later, to control the LEDs 42 to 45 so that a predetermined color balance can be maintained. On the other hand, if the sensor values from the optical sensors 42*b* to 45*b* are smaller than the predetermined value, the control section 41 controls the duty cycles of PWM pulses to control the LEDs 42 to 45 so that a predetermined color balance can be maintained.

Based on the brightness control information from the video processor 20, the control section 41 controls amounts of light from the respective LEDs 42 to 45 while a light emission amount (light amount) ratio of the respective LEDs 42 to 45 is maintained so that an optimum color balance can be obtained. For example, the control section 41 calculates light adjustment information corresponding to a light amount value to be set for the G-LED 43 according to the brightness control information from the video processor 20, and calculates light adjustment information for the other LEDs 42, 44 and 45 according to the light amount value of the G-LED 43 so that a predetermined light amount ratio is achieved.

In other words, the control section 41 controls the light amount value of the G-LED 43 based on the brightness control information from the video processor 20. Then, the control section 41 controls a light amount value of each of the other LEDs 42, 44 and 45 based on a detection result from the optical sensor 43*b* for the G-LED 43 and a detection result from the optical sensor 42*b*, 44*b* or 45*b* for the relevant color so that a predetermined color balance is achieved (a light amount ratio between G and the relevant color reaches a target ratio).

The color balance ratio controlled as described above can be expressed by (Equation 1) where green light, which most contributes to a luminance of light, is set as a reference.

$$LR:LB:LG:LV=\alpha:\beta:1:\gamma \qquad \text{(Equation 1)}$$

Figure 2:
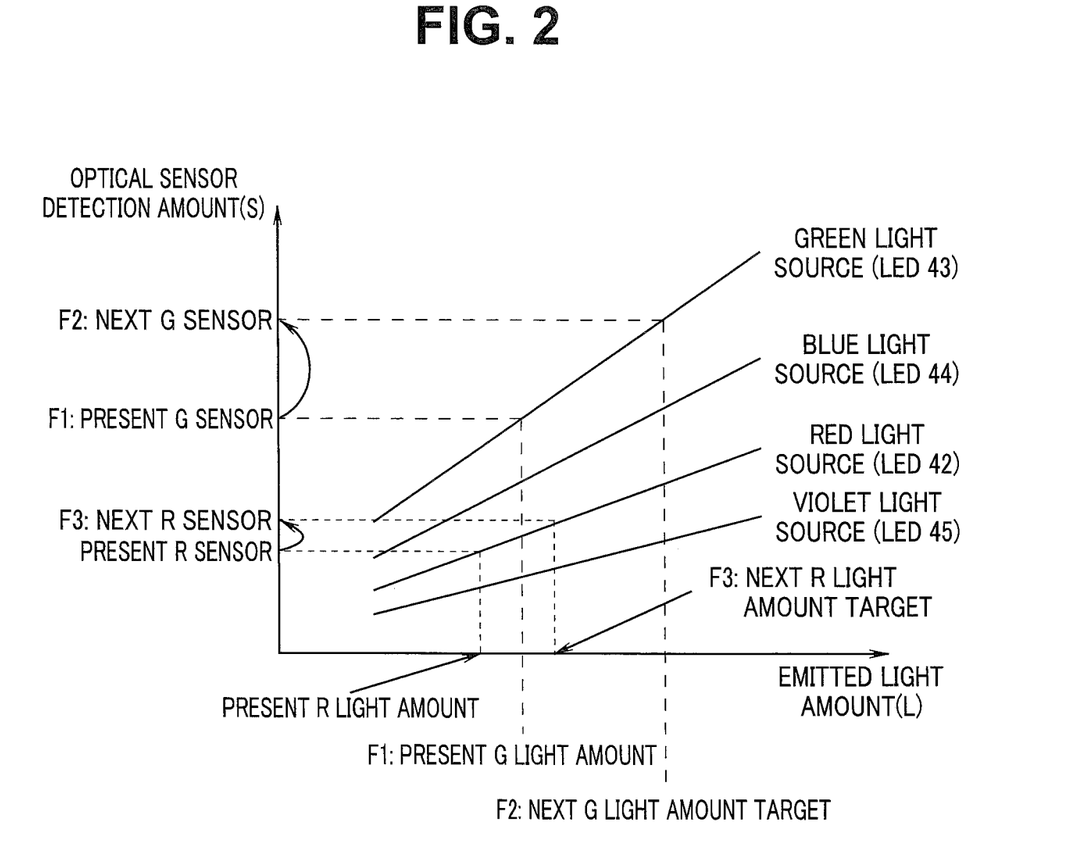
FIG. 2 is a diagram illustrating respective relationships between amounts of detection by optical sensors 42b to 45b and emitted light amounts, for respective LEDs 42 to 45.

A method for controlling a color balance ratio as in (Equation 1) by means of the control section 41 will be described below. FIG. 2 is a diagram indicating respective relationships between amounts of detection by the optical sensors 42*b* to 45*b* and emitted light amounts, for the respective LEDs 42 to 45.

The linear relationships for the respective LEDs 42 to 45 indicated in FIG. 2 can be expressed by (Equation 2) to (Equation 5) where (S) is an optical sensor detection amount, (L) is an emitted light amount, (A) is an inclination and (B) is an intercept.

$$S\text{ RED} = A\text{ RED} \times L\text{ RED} + B\text{ RED} \quad \text{(Equation 2)}$$

$$S\text{ BLUE} = A\text{ BLUE} \times L\text{ BLUE} + B\text{ BLUE} \quad \text{(Equation 3)}$$

$$S\text{ GREEN} = A\text{ GREEN} \times L\text{ GREEN} + B\text{ GREEN} \quad \text{(Equation 4)}$$

$$S\text{ VIOLET} = A\text{ VIOLET} \times L\text{ VIOLET} + B\text{ VIOLET} \quad \text{(Equation 5)}$$

According to (Equation 1) to (Equation 5), relationships in detection amount between the optical sensor 43b for green light and the optical sensors 42b, 44b and 45b for the other LEDs 42, 44 and 45 can be expressed by (Equation 6) to (Equation 8).

$$S\text{ RED} = \alpha \times (A\text{ RED}/A\text{ GREEN}) \times (S\text{ GREEN} - B\text{ GREEN}) + B\text{ RED} \quad \text{(Equation 6)}$$

$$S\text{ BLUE} = \beta \times (A\text{ BLUE}/A\text{ GREEN}) \times (S\text{ GREEN} - B\text{ GREEN}) + B\text{ BLUE} \quad \text{(Equation 7)}$$

$$S\text{ VIOLET} = \gamma \times (A\text{ VIOLET}/A\text{ GREEN}) \times (S\text{ GREEN} - B\text{ GREEN}) + B\text{ VIOLET} \quad \text{(Equation 8)}$$

In the memory 41a of the control section 41, information indicating a relationship between a target value for an intensity detected by the optical sensor 43b and a target value for an intensity detected by each of the optical sensors 42b, 44b and 45b ((Equation 6) to (Equation 8)) and information on a minimum value of the intensity detected by each of the optical sensors 42b to 45b are stored. Here, the memory 41a may store a plurality of pieces of information on (Equation 6) to (Equation 8) for respective endoscopes 10 to be connected to the light source apparatus 40 or respective different observation modes. Also, the memory 41a may store information indicated in (Equation 1) to (Equation 5) instead of information indicated in (Equation 6) to (Equation 8). Then, the control section 41 may calculate information indicated in (Equation 6) to (Equation 8) based on the information indicated in (Equation 1) to (Equation 5).

When color balance ratio control is performed, the control section 41, which serves as a determination section, determines whether or not the intensities detected by the optical sensors 42b to 45b exceed the respective minimum values stored in the memory 41a. Here, in the memory 41a, the information indicated in (Equation 6) to (Equation 8) and information on the intensity detected by the optical sensor 43b may be stored. Then, when the color balance ratio control is performed, the control section 41 may determine whether or not the intensity detected by the optical sensor 43b exceeds the relevant minimum value of the intensity stored in the memory 41a.

If the intensity detected by the optical sensor 43b exceeds the minimum value of the intensity stored in the memory 41a, the control section 41 performs color balance ratio control using the optical sensors 42b to 45b.

In the color balance ration control, with the green light set as a reference, the control section 41 performs three flows F1, F2 and F3 below in a single control to control the light amounts of the other colors. Here, although light amount control of the red light from the LED 42 will be described as an example, light amount control for each of the blue light and the violet light is similar to the above control for the red light. Note that the flows F1 to F3 correspond to F1 to F3 indicated in FIG. 2, which indicate what the control is like based on the relationship in FIG. 2.

First, as the flow F1, the control section 41 acquires a present light amount of the G-LED 43 (green light) and a present detection amount of the optical sensor 43b.

Next, as the flow F2, the control section 41 acquires a target value for the detection amount of the optical sensor 43b, from a next target light amount for the G-LED 43.

Lastly, as the flow F3, the control section 41, which serves as a calculation section, calculates a target value for the detection amount of the optical sensor 42b for the R-LED 42 (red light) using the acquired target value for the detection amount of the optical sensor 43b and (Equation 6).

For the B-LED 44 (blue light) and the V-LED 45 (violet light), also, the control section 41 increases/decreases respective control values (current values for drive signals) for the B-LED 44 and the V-LED 45 using (Equation 7) and (Equation 8) so that the detection amounts of the optical sensor 44b and the optical sensor 45b reach respective target values, to control the light amounts.

The control section 41, which serves as a light amount control section, performs the flow F2 and the flow F3 simultaneously in a single control, and thus performs light amount control for red light of the R-LED 42, blue light of the B-LED 44 and violet light of the V-LED 45 simultaneously with light amount control for the green light of the G-LED 43, which is reference light. Consequently, a predetermined color balance ratio can be kept without a color balance ratio being lost immediately after light amount variation.

On the other hand, if the intensity detected by the optical sensor 43b is smaller than the minimum value of the intensity stored in the memory 41a, the control section 41 controls the PWM duty cycles while the current values of the respective LEDs 42 to 45 are maintained. Here, if the intensity detected by the optical sensor 43b is smaller than the minimum value of the intensity stored in the memory 41a, the control section 41 may perform control so as to decrease the number of pulses while the current values of the LEDs 42 to 45 are maintained.

Although the present embodiment has been described in terms of a case where with the green light, which most contributes to a luminance of light, set as a reference, light amounts of the other colors are controlled, the color set as a reference is not limited to the green light and may be any of the other colors.

Figure 3:
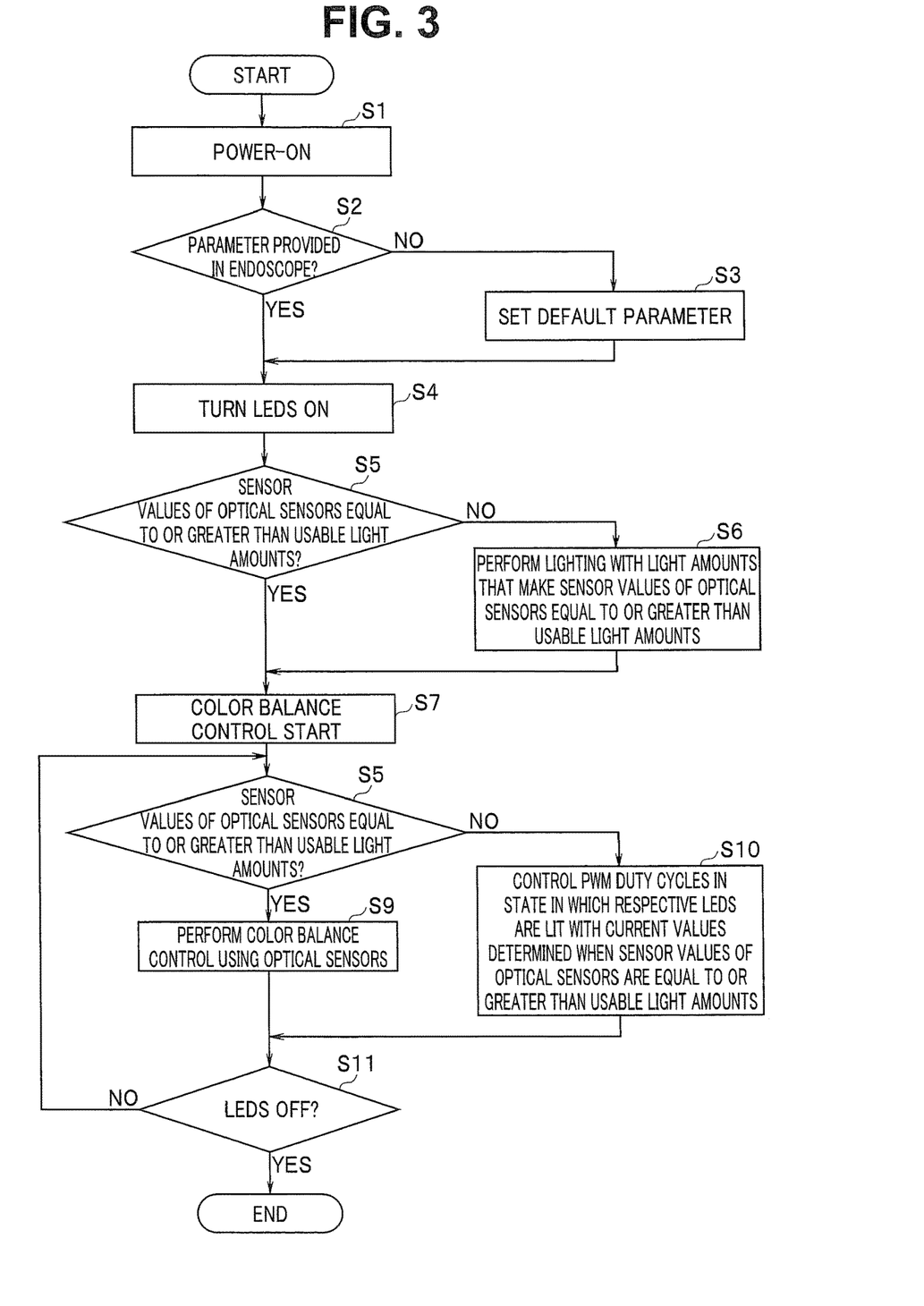
FIG. 3 is a flowchart for describing color balance ratio control performed by an endoscope apparatus.

Here, operation of the endoscope apparatus configured as described above will be described. FIG. 3 is a flowchart for describing color balance ratio control performed by the endoscope apparatus.

First, the endoscope apparatus 1 is powered on (step S1), whether or not a parameter is provided in an endoscope 10 is determined (step S2). The parameter is information on a target color balance ratio indicated in (Equation 1) described above and stored in, e.g., a non-illustrated memory in the endoscope 10.

If it is determined that no parameter is provided in the endoscope 10, a result of the determination is "NO", and a default parameter is set (step S3) and the LEDs 42 to 45 are tuned on (step S4). On the other hand, if it is determined that a parameter is provided in the endoscope 10, the result of the determination is "YES", and the parameter is set, and in step S4, the LEDs 42 to 45 are turned on.

Next, whether or not sensor values from the optical sensors 42b to 45b are equal to or greater than usable light amounts is determined (step S5). Here, although whether or not sensor values of the optical sensors 42b to 45b are equal to or greater than usable light amounts is determined in step S5, the present embodiment is not limited to this case, and, for example, whether or not PWM duty cycles are equal to or greater than a predetermined value may be determined. If it is determined that the sensor values of the optical sensors 42b to 45b are neither equal to nor greater than the usable light amounts, a result of the determination is "NO" and the LEDs 42 to 45 are lit with respective light amounts that make the sensor values of the optical sensors 42b to 45b be equal to or greater than the usable light amounts (step S6), and color balance control is started (step S7). On the other hand, if it is determined that the sensor values of the optical sensors 42b to 45b are equal to or greater than the usable light amounts, the result of the determination is "YES", and the operation proceeds to step S7 and color balance control is started.

Upon the start of the color balance control, whether or not the sensor values of the optical sensors 42b to 45b are equal to or greater than the usable light amounts is determined (step S8). Here, although in step S8, whether or not the sensor values of the optical sensors 42b to 45b are equal to or greater than the usable light amounts is determined, the present embodiment is not limited to this case, and, for example, whether or not the PWM duty cycles are equal to or greater than a predetermined value may be determined. If it is determined that the sensor values of the optical sensors 42b to 45b are equal to or greater than the usable light amounts, a result of the determination is "YES", and color balance control is performed using the optical sensors 42b to 45b (step 9). On the other hand, if it is determined that the sensor values of the optical sensors 42b to 45b are neither equal to nor greater than the usable light amounts, the result of the determination is "NO", the PWM duty cycles are controlled in a state in which the respective LEDs 42 to 45 are lit with respective current values determined when the sensor values of the optical sensors 42b to 45b are equal to or greater than the usable light amounts, in order to continuously control brightness (step S10).

Next, upon step S9 or S10 being performed, whether or not the LEDs 42 to 45 are off is determined (step S11). If it is determined that the LEDs 42 to 45 are not off, a result of the determination is "NO", and the operation returns to step S8 and processing similar to the above is repeated. On the other hand, if it is determined that the LEDs 42 to 45 are off, the result of the determination is "YES" and the color balance ratio control is ended.

As described above, if the sensor values of the optical sensors 42b to 45b are equal to or greater than the usable light amounts, the endoscope apparatus 1 increases/decreases drive current values for the LEDs 42, 44 and 45 based on a detection amount of green light detected by the optical sensor 43b and (Equation 6) to (Equation 8) so that detection amounts of the optical sensors 42b, 44b and 45b for the LEDs 42, 44 and 45 reach respective target values, to control the light amounts of the LEDs 42, 44 and 45. Consequently, light amount control for the LEDs 42, 44 and 45 is performed simultaneously with light amount control for the LED 43 for the green light, which is a reference color, to maintain a color balance.

On the other hand, if the sensor values of the optical sensors 42b to 45b are smaller than the usable light amounts, the endoscope apparatus 1 changes the PWM duty cycles or the numbers of pulses while the current values of the respective LEDs 42 to 45 determined when the sensor values of the optical sensors 42b to 45b are equal to or greater than the usable light amounts are maintained, to control the light amounts of the LEDs 42 to 45.

Consequently, the endoscope apparatus according to the present embodiment is capable of, where a light source configured to multiplex and output light from a plurality of semiconductor light-emitting elements is provided, even if sensor values from optical sensors are unusable, properly controlling a color balance of outputted light.

Second Embodiment

Figure 4:
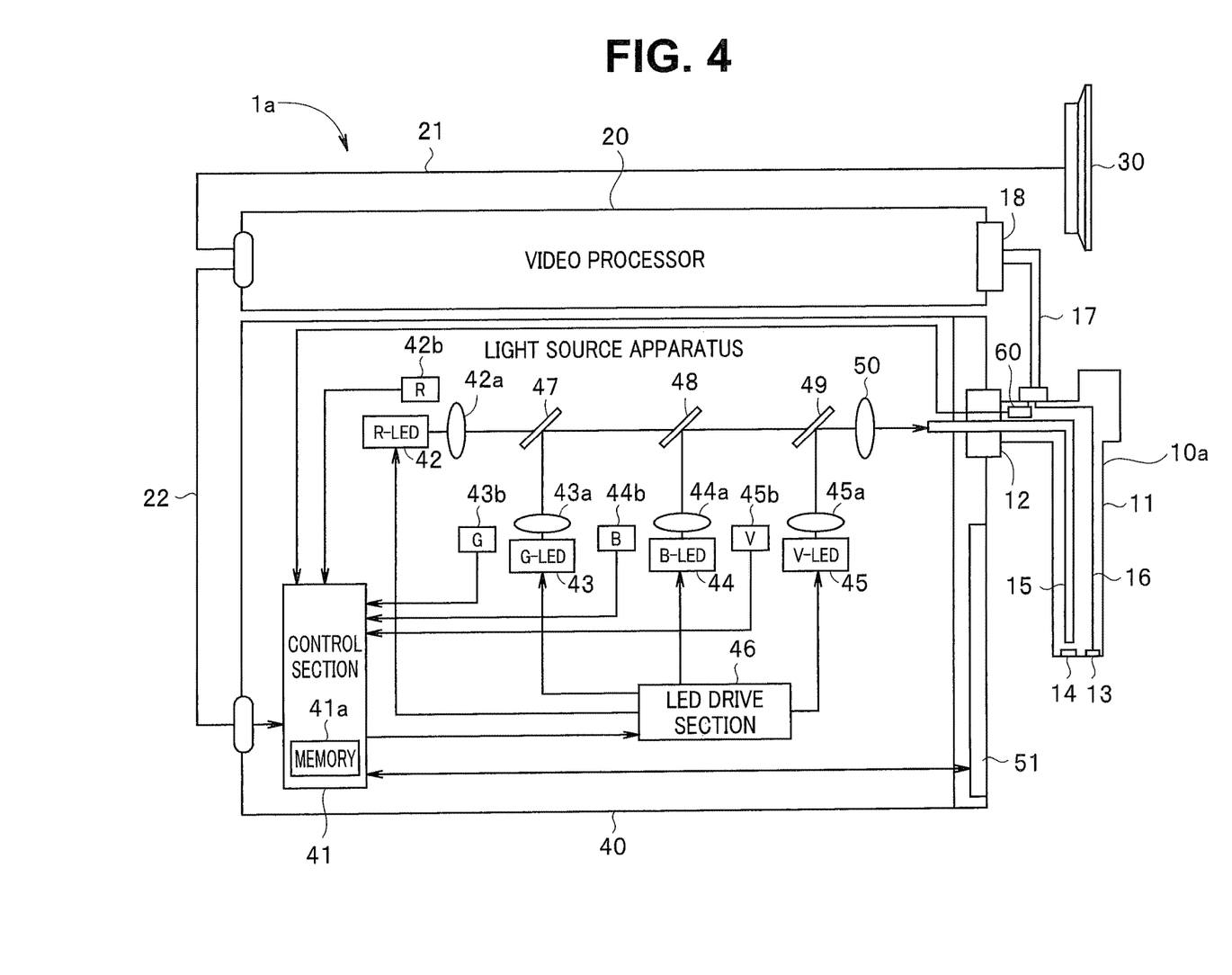
FIG. 4 is a block diagram illustrating a configuration of an endoscope apparatus according to a second embodiment.

FIG. 4 is a block diagram illustrating a configuration of an endoscope apparatus according to a second embodiment. In FIG. 4, components that are similar to the components in FIG. 1 are provided with reference numerals that are the same as the reference numerals in FIG. 1, and description of such components will be omitted.

As illustrated in FIG. 4, the endoscope apparatus 1a includes an endoscope 10a instead of the endoscope 10 in FIG. 1. The endoscope 10a is configured by adding a memory 60 to the endoscope 10 in FIG. 1.

In the memory 60, optical characteristic information according to a type of the endoscope 10a is stored. The optical characteristic information includes illumination optical characteristics (including a light transmission characteristic of a light guide) and objective optical characteristics (including a spectral sensitivity of an image pickup unit).

Upon connection of the endoscope 10a to a video processor 20 and a light source apparatus 40, the video processor 20 and the light source apparatus 40 acquire the optical characteristic information from the memory 60 by means of communication with the endoscope 10a.

Based on the optical characteristic information, the video processor 20 sets a hue parameter to be used for image processing. Also, based on the optical characteristic information, the light source apparatus 40 sets a spectral characteristic. The hue parameter and the spectral characteristic information can be communicated between the video processor 20 and the light source apparatus 40 via a cable 22.

If no optical characteristic information is stored in the memory 60 of the endoscope 10a or if no memory 60 is provided in the endoscope 10a, the video processor 20 sets the hue parameter to a predetermined value (default value).

Likewise, if no optical characteristic information is stored in the memory 60 of the endoscope 10a or if no memory 60 is provided in the endoscope 10a, the light source apparatus 40 sets the spectral characteristic to a predetermined value (default value).

Here, if no optical characteristic information is stored in the memory 60 of the endoscope 10a or if no memory 60 is provided in the endoscope 10a, the video processor 20 and the light source apparatus 40 may acquire a type of an imager (type of an image pickup device 13) in the endoscope 10a and set the hue parameter and the spectral characteristic according to the type of the imager, respectively.

Also, the video processor 20 and the light source apparatus 40 may set the hue parameter and the spectral characteristic according to an observation mode (normal observation or special observation), based on the optical characteristic information or the type of the imager.

Also, the video processor 20 and the light source apparatus 40 may set the hue parameter and the spectral characteristic according to a combination of the connected endoscope 10a and a type of lamps installed in the light source apparatus 40 (for example, halogen lamps, metal halide lamps, LEDs or LDs), respectively.

Also, the video processor 20 and the light source apparatus 40 may set the hue parameter and the spectral characteristic according to a combination of the connected endoscope 10a and lighting time of the lamps installed in the light source apparatus 40, respectively.

Also, if the light source apparatus 40 includes a plurality of light sources of different wavelengths, the light source apparatus 40 may set the spectral characteristic by changing light emission intensities of the plurality of light sources.

Also, the video processor 20 and the light source apparatus 40 may have a timing for setting the hue parameter and the spectral characteristic when a white balance is acquired, respectively, and adjust the hue parameter and the spectral characteristic with information on a picked-up image of an object at that time also taken into consideration.

The video processor 20 and the light source apparatus 40 store the set hue parameter information and the set spectral characteristic information in the memory 60 of the endoscope 10*a*, respectively, by means of communication with the endoscope 10*a*. Here, the hue parameter information and the spectral characteristic information are stored in the memory 60 in association with relation to specific information (e.g., S/N) of the video processor 20 and the light source apparatus 40. Then, the video processor 20 and the light source apparatus 40 may read the hue parameter information and the spectral characteristic information from the memory 60 and set the hue parameter information and the spectral characteristic information, respectively, in next activation.

Note that the respective steps in the flowchart in the present description may be performed in an order that is different from the above order, a plurality of steps in the respective steps may be performed simultaneously, or may be performed in a different order each time the operation is performed as long as such manners of the steps being performed do not impair the nature of each of the steps.

The present invention is not limited to the above-described embodiments, and various changes, alterations and the like are possible without departing from the spirit of the present invention.

What is claimed is:

1. An endoscope apparatus comprising:
   a first semiconductor light source configured to generate light according to a current value of an inputted drive signal;
   a first sensor configured to receive a part of the light generated from the first semiconductor light source and detect a first intensity; and
   a controller comprising hardware, the controller being configured to:
      store a minimum detectable value for the first intensity;
      if the first intensity detected by the first sensor exceeds the stored minimum detectable value, control the current value of the drive signal to the first semiconductor light source based on the first intensity detected by the first sensor; and
      if the first intensity detected by the first sensor does not exceed the minimum detectable value, perform control so as to make the current value of the drive signal to the first semiconductor light source constant to provide pulsed light emission and change one of a duty cycle or a number of pulses to perform light adjustment;
   a second semiconductor light source configured to generate light having a wavelength that is different from a wavelength of the first semiconductor light source; and
   a second sensor configured to receive a part of the light generated from the second semiconductor light source and detect a second intensity, wherein;
   the controller is further configured to:
      if the first intensity detected by the first sensor is smaller than the minimum detectable value, control so as to make the current value of the drive signal inputted to the first semiconductor light source and a current value of the drive signal inputted to the second semiconductor light source constant to provide pulsed light emission and change respective duty cycles and respective numbers of pulses to perform light adjustment;
      store information representing a relationship between a target value for the first intensity detected by the first sensor and a target value for the second intensity detected by the second sensor;
      calculate a target value for the second intensity detected by the second sensor, the target value corresponding to the first intensity detected by the first sensor, from the first intensity detected by the first sensor and the stored information; and
      if the first intensity detected by the first sensor is equal to or greater than the minimum detectable value, control driving of the second semiconductor light source so that the second intensity detected by the second sensor reaches e calculated target value.

2. The endoscope apparatus according to claim 1, further comprising an optical member configured to multiplex and output the light generated from the first semiconductor and the light generated from the second semiconductor light source,
   wherein the stored information is information that enables the controller to calculate a target value for an intensity detected as a second detection value, the target value preventing change in hue of output light outputted from the optical member when the first intensity detected by the first sensor varies.

3. The endoscope apparatus according to claim 1, wherein information representing a relationship between the target value for the first intensity detected by the first sensor and the target value for the second intensity detected by the second sensor, for each of a plurality of endoscopes to be connected to the endoscope apparatus or each of a plurality of different observation modes.

* * * * *

UNITED STATES PATENT AND TRADEMARK OFFICE
CERTIFICATE OF CORRECTION

PATENT NO. : 10,610,082 B2
APPLICATION NO. : 15/473927
DATED : April 7, 2020
INVENTOR(S) : Satoshi Tanaka et al.

Page 1 of 1

It is certified that error appears in the above-identified patent and that said Letters Patent is hereby corrected as shown below:

In the Claims

Column 10, Claim 1, Line 34 should read:
second sensor reaches the calculated target value.

Signed and Sealed this
Twentieth Day of October, 2020

Andrei Iancu
*Director of the United States Patent and Trademark Office*